(12) United States Patent
Hashimoto et al.

(10) Patent No.: US 11,617,819 B2
(45) Date of Patent: Apr. 4, 2023

(54) EXTRACORPOREAL CIRCULATION MANAGEMENT DEVICE WITH HEARTBEAT SYNCHRONIZATON

(71) Applicant: TERUMO KABUSHIKI KAISHA, Tokyo (JP)

(72) Inventors: Tomoaki Hashimoto, Kanagawa (JP); Tsuyoshi Hasegawa, Kanagawa (JP); Ryohei Katsuki, Kanagawa (JP); Yuuki Hara, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1122 days.

(21) Appl. No.: 16/113,386

(22) Filed: Aug. 27, 2018

(65) Prior Publication Data

US 2018/0369465 A1 Dec. 27, 2018

Related U.S. Application Data

(63) Continuation of application No. PCT/JP2017/006778, filed on Feb. 23, 2017.

(30) Foreign Application Priority Data

Mar. 17, 2016 (JP) .............................. JP2016-054036

(51) Int. Cl.
  *A61M 1/36* (2006.01)
  *A61M 60/523* (2021.01)
  (Continued)

(52) U.S. Cl.
  CPC ........ *A61M 1/3667* (2014.02); *A61M 1/3639* (2013.01); *A61M 60/109* (2021.01);
  (Continued)

(58) Field of Classification Search
  CPC .. A61M 60/562; A61M 60/50; A61M 60/113; A61M 1/3639; A61M 1/3667;
  (Continued)

(56) References Cited

U.S. PATENT DOCUMENTS 9,125,977 B2 9/2015 Nishimura et al.
2002/0173693 A1* 11/2002 Landesberg ........ A61M 60/441
  600/16

(Continued)

FOREIGN PATENT DOCUMENTS

JP 2888609 B2 5/1999
JP 3138023 B2 2/2001
(Continued)

OTHER PUBLICATIONS

PCT/JP2017/006778, International Search and Opinion Report, dated Apr. 19, 2017.
(Continued)

*Primary Examiner* — Jessica Arble
(74) *Attorney, Agent, or Firm* — MacMillan, Sobanski & Todd, LLC

(57) ABSTRACT

An extracorporeal circulation management device pumps blood in synchronization with heartbeats of a patient based on measurements of blood flow. Maximum and minimum blood flow measurement samples are compared with upper and lower threshold values to identify candidate timing for a systolic phase and diastolic phase of the heartbeat. During pulsatile pumping of the blood using the candidate timing, differences in the pulsatile flow measurements are determined. Based on the size of the difference, a final correction may be made to identification of the systolic and diastolic phases, and the corrected phase information is used to start and stop the motor unit.

7 Claims, 15 Drawing Sheets

(51) Int. Cl.
*A61M 60/113* (2021.01)
*A61M 60/408* (2021.01)
*A61M 60/857* (2021.01)
*A61M 60/232* (2021.01)
*A61M 60/546* (2021.01)
*A61M 60/109* (2021.01)

(52) U.S. Cl.
CPC ........ *A61M 60/113* (2021.01); *A61M 60/232* (2021.01); *A61M 60/408* (2021.01); *A61M 60/523* (2021.01); *A61M 60/546* (2021.01); *A61M 60/857* (2021.01); *A61M 2205/3334* (2013.01); *A61M 2205/50* (2013.01); *A61M 2230/06* (2013.01)

(58) Field of Classification Search
CPC ...... A61M 2205/3334; A61M 2205/50; A61M 2230/06
See application file for complete search history.

(56) References Cited

U.S. PATENT DOCUMENTS

| | | | |
|---|---|---|---|
| 2008/0249456 A1* | 10/2008 | Inamori | A61M 60/515 |
| | | | 604/6.14 |
| 2015/0367048 A1 | 12/2015 | Brown et al. | |
| 2017/0239407 A1* | 8/2017 | Hayward | A61M 60/523 |

FOREIGN PATENT DOCUMENTS

| | | |
|---|---|---|
| JP | 2009297174 A | 12/2009 |
| JP | 2013252365 A | 12/2013 |

OTHER PUBLICATIONS

European Patent Office, 17766271.5 / PCT/JP2017006778, dated Oct. 2, 2019.

\* cited by examiner

| 30 |
|---|
| FLOW RATE DATA STORAGE UNIT (STORE FLOW RATE VALUE DATA TOGETHER WITH TIME DATA TO WHICH FLOW RATE VALUE DATA CORRESPONDS) — 31 |
| FIRST DETERMINATION TARGET FLOW RATE VALUE DATA EXTRACTION PROCESSING UNIT (PROGRAM) (SELECT THREE OLDEST ITEMS IN CHRONOLOGICAL TIME SERIES ORDER FROM FLOW RATE VALUE DATA OF "FLOW RATE DATA STORAGE UNIT", AND STORE THREE ITEMS TOGETHER WITH CORRESPONDING TIME DATA IN "DETERMINATION TARGET FLOW RATE VALUE DATA STORAGE UNIT") — 32 |
| DETERMINATION TARGET FLOW RATE VALUE DATA STORAGE UNIT (FOR EXAMPLE, X1, X2, X3) — 33 |
| MAXIMUM CANDIDATE VALUE DATA DETERMINATION PROCESSING UNIT (PROGRAM) (REFER TO "DETERMINATION TARGET FLOW RATE VALUE DATA STORAGE UNIT", SELECT THREE OLDEST FLOW RATE VALUE ITEMS IN CHRONOLOGICAL TIME SERIES ORDER, DETERMINE WHETHER OR NOT SECOND FLOW RATE VALUE IS GREATER THAN FLOW RATE VALUE OF TWO EARLIER AND LATER ITEMS, AND WHEN DETERMINED AS GREATER THAN FLOW RATE VALUE OF TWO EARLIER AND LATER ITEMS, STORE SECOND FLOW RATE VALUE TOGETHER WITH CORRESPONDING TIME DATA IN "MAXIMUM CANDIDATE VALUE DATA STORAGE UNIT") — 34 |
| MAXIMUM CANDIDATE VALUE DATA STORAGE UNIT (FOR EXAMPLE, STORE FLOW RATE VALUE OF X2 AND CORRESPONDING TIME DATA) — 35 |
| THRESHOLD VALUE DATA STORAGE UNIT (STORE "UPPER THRESHOLD VALUE DATA" FOR DETERMINING FLOW RATE VALUE AS MAXIMUM VALUE AND "LOWER THRESHOLD VALUE DATA" FOR DETERMINING FLOW RATE VALUE AS MINIMUM VALUE) — 37 |
| MAXIMUM VALUE DATA DETERMINATION PROCESSING UNIT (PROGRAM) (DETERMINE WHETHER OR NOT "MAXIMUM CANDIDATE VALUE DATA" OF "MAXIMUM CANDIDATE VALUE DATA STORAGE UNIT" IS GREATER THAN "UPPER THRESHOLD VALUE" OF "THRESHOLD VALUE DATA STORAGE UNIT", ASSOCIATE "MAXIMUM CANDIDATE VALUE DATA" GREATER THAN "UPPER THRESHOLD VALUE" WITH CORRESPONDING TIME DATA AS "MAXIMUM VALUE DATA", AND STORE ASSOCIATED DATA IN "MAXIMUM VALUE STORAGE UNIT") — 36 |

41 MAXIMUM VALUE DATA STORAGE UNIT (FOR EXAMPLE, X2 AND CORRESPONDING TIME DATA)

42 SECOND DETERMINATION TARGET FLOW RATE VALUE DATA EXTRACTION PROCESSING UNIT (PROGRAM) (SELECT THREE OLDEST ITEMS IN CHRONOLOGICAL TIME SERIES ORDER FROM FLOW RATE VALUE DATA OF "FLOW RATE VALUE DATA STORAGE UNIT" EXCEPT FOR DATA ASSOCIATED WITH OLDEST TIME DATA OF "DETERMINATION TARGET FLOW RATE VALUE DATA STORAGE UNIT", AND STORES THREE OLDEST ITEMS TOGETHER WITH CORRESPONDING TIME DATA IN "DETERMINATION TARGET FLOW RATE VALUE DATA STORAGE UNIT". IN THIS CASE, DELETE PRE-STORED DATA.)

43 MINIMUM CANDIDATE VALUE DATA DETERMINATION PROCESSING UNIT (PROGRAM) (REFER TO "DETERMINATION TARGET FLOW RATE VALUE DATA STORAGE UNIT", SELECT THREE OLDEST ITEMS IN CHRONOLOGICAL TIME SERIES ORDER, DETERMINE WHETHER OR NOT SECOND FLOW RATE VALUE IS SMALLER THAN FLOW RATE VALUE OF TWO EARLIER AND LATER ITEMS, AND WHEN DETERMINED AS SMALLER THAN FLOW RATE VALUE OF TWO EARLIER AND LATER ITEMS, STORE SECOND FLOW RATE VALUE TOGETHER WITH CORRESPONDING TIME DATA IN "MINIMUM CANDIDATE VALUE DATA STORAGE UNIT")

44 MINIMUM CANDIDATE VALUE DATA STORAGE UNIT (FOR EXAMPLE, STORE FLOW RATE VALUE OF X2 AND CORRESPONDING TIME DATA)

45 MINIMUM VALUE DATA DETERMINATION PROCESSING UNIT (PROGRAM) (DETERMINE WHETHER OR NOT "MINIMUM CANDIDATE VALUE DATA" OF "MINIMUM CANDIDATE VALUE DATA STORAGE UNIT" IS SMALLER THAN "LOWER THRESHOLD VALUE" OF "THRESHOLD VALUE DATA STORAGE UNIT", ASSOCIATE "MINIMUM CANDIDATE VALUE DATA" SMALLER THAN "LOWER THRESHOLD VALUE" WITH CORRESPONDING TIME DATA AS "MINIMUM VALUE DATA", AND STORE "MINIMUM VALUE DATA" IN "MINIMUM VALUE STORAGE UNIT")

46 MINIMUM VALUE DATA STORAGE UNIT (FOR EXAMPLE, STORE FLOW RATE VALUE OF X9 AND CORRESPONDING TIME DATA)

51
HEARTBEAT NOISE DELETION PROCESSING UNIT (PROGRAM)
(REFER TO "MAXIMUM VALUE DATA STORAGE UNIT" AND "MINIMUM VALUE DATA STORAGE UNIT")
1) EXTRACT ITEMS IN CHRONOLOGICAL TIME SERIES ORDER, AND STORE OLDEST "MINIMUM VALUE DATA THEREOF" AS "FIRST HEARTBEAT START TIME DATA" IN "HEARTBEAT CYCLE DATA STORAGE UNIT"
2) SUBSEQUENTLY, STORE "MAXIMUM VALUE" MOST PROXIMATE IN TIME SERIES TO "MINIMUM VALUE DATA" AT "FIRST HEARTBEAT START TIME" AND "TIME DATA THEREOF" AS "FIRST HEARTBEAT MAXIMUM TIME DATA" IN "HEARTBEAT CYCLE DATA STORAGE UNIT"
3) SUBSEQUENTLY, STORE "MINIMUM VALUE DATA" MOST PROXIMATE IN TIME SERIES TO "TIME DATA" OF "MAXIMUM VALUE" OF "FIRST HEARTBEAT" WHICH IS "FIRST HEARTBEAT MAXIMUM VALUE DATA" AND "TIME DATA THEREOF", AS "SECOND HEARTBEAT START TIME DATA" IN "HEARTBEAT CYCLE DATA STORAGE UNIT"
4) SUBSEQUENTLY, STORE "MAXIMUM VALUE" MOST PROXIMATE IN TIME SERIES TO "MINIMUM VALUE DATA" AT "SECOND HEARTBEAT START TIME" AND "TIME DATA THEREOF" AS "SECOND HEARTBEAT MAXIMUM TIME DATA" IN "HEARTBEAT CYCLE DATA STORAGE UNIT"
5) PERFORM SIMILAR PROCESSING AFTER THIRD HEARTBEAT START TIME, AND PERFORM PROCESSING ON PREDETERMINED PERIOD DATA STORED IN "MAXIMUM VALUE DATA STORAGE UNIT" AND "MINIMUM VALUE DATA STORAGE UNIT")

52
HEARTBEAT CYCLE DATA STORAGE UNIT (STORE "FIRST HEARTBEAT START TIME DATA", "FIRST HEARTBEAT MAXIMUM TIME DATA", "SECOND HEARTBEAT START TIME DATA", AND "SECOND HEARTBEAT MAXIMUM TIME DATA")

53
DELAY DATA STORAGE UNIT (STORE DELAY TIME ($\Delta T1$) CORRESPONDING TO TUBE LENGTH)

54
TUBE LENGTH DATA STORAGE UNIT (STORE TUBE LENGTH DATA BETWEEN ARTIFICIAL LUNG AND PATIENT)

61 CORRECTED HEARTBEAT CYCLE DATA GENERATION PROCESSING UNIT (PROGRAM) (REFER TO "DELAY DATA STORAGE UNIT", IDENTIFY "DELAY TIME" CORRESPONDING TO "TUBE LENGTH DATA" OF "TUBE LENGTH DATA STORAGE UNIT", CORRECT TIME DATA OF "FIRST HEARTBEAT START TIME DATA" OF "HEARTBEAT CYCLE DATA STORAGE UNIT", AND STORE CORRECTED TIME DATA AS "CORRECTED FIRST HEARTBEAT START TIME DATA" IN "CORRECTED HEARTBEAT CYCLE DATA STORAGE UNIT")

62 CORRECTED HEARTBEAT CYCLE DATA STORAGE UNIT (STORE "CORRECTED FIRST HEARTBEAT START TIME DATA", "CORRECTED FIRST HEARTBEAT MAXIMUM TIME DATA", "CORRECTED SECOND HEARTBEAT START TIME DATA", AND "CORRECTED SECOND HEARTBEAT MAXIMUM TIME DATA")

64 BLOOD SUPPLY AMOUNT DATA STORAGE UNIT (DATA OF BLOOD SUPPLY AMOUNT SUPPLIED BY CENTRIFUGAL PUMP PERFORMING BLOOD SUPPLY ONCE)

63 BLOOD SUPPLY OPERATION INSTRUCTION PROCESSING UNIT (PROGRAM) (BASED ON "CORRECTED FIRST HEARTBEAT START TIME DATA" OF "CORRECTED HEARTBEAT CYCLE DATA STORAGE UNIT" AND BLOOD SUPPLY AMOUNT DATA OF "BLOOD SUPPLY AMOUNT DATA STORAGE UNIT", CONTROL DRIVE MOTOR, STOP BLOOD SUPPLY TO ARTERY, AND PERFORM BLOOD SUPPLY AS MUCH AS PREDETERMINED AMOUNT)

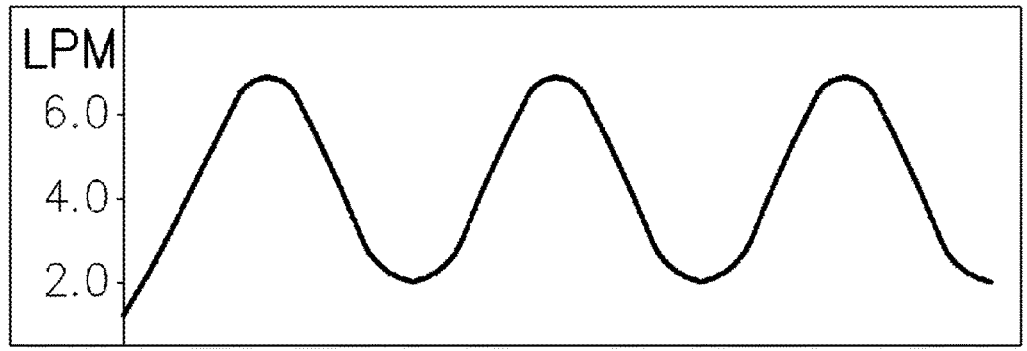
Fig. 14
Fig. 17A
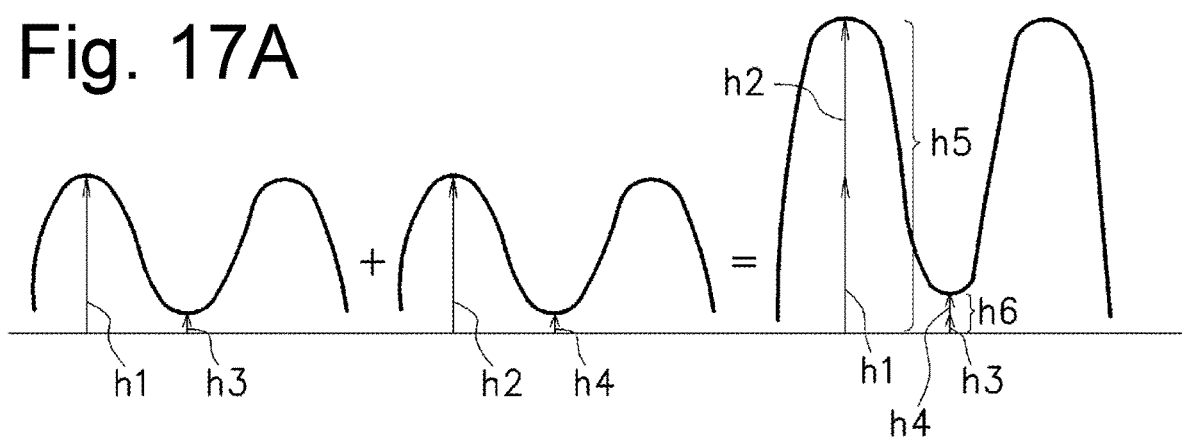
Fig. 17B
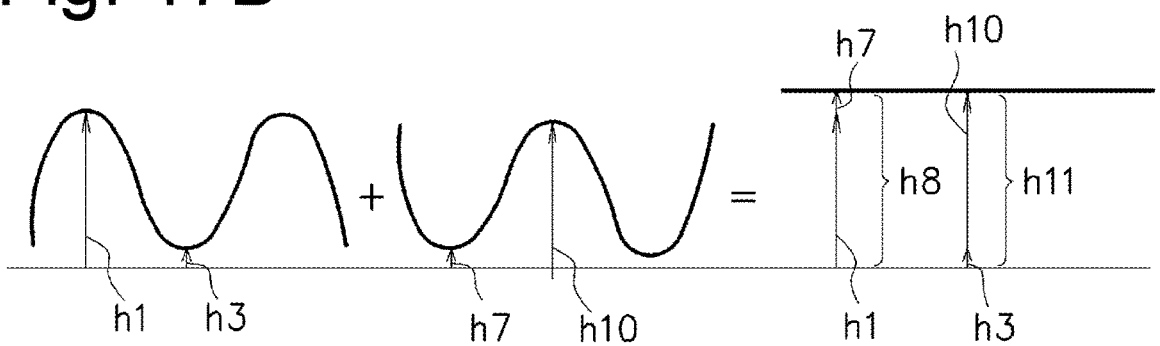

| | SAMPLE VALUE | UPPER THRESHOLD VALUE | LOWER THRESHOLD VALUE | MAXIMUM VALUE | MINIMUM VALUE | ASSESSMENT |
|---|---|---|---|---|---|---|
| 1 | 1.0 | 6.7 | 3.3 | — | MINIMUM VALUE | FIRST HEARTBEAT START |
| 2 | 10.0 | 6.7 | 3.3 | MAXIMUM VALUE | — | 1 |
| 3 | 5.0 | 6.7 | 3.3 | — | — | 1 |
| 4 | 6.5 | 6.7 | 3.3 | — | — | 1 |
| 5 | 9.0 | 6.7 | 3.3 | — | — | 1 |
| 6 | 9.0 | 6.7 | 3.3 | — | — | 1 |
| 7 | 6.5 | 6.7 | 3.3 | — | — | 1 |
| 8 | 7.0 | 6.7 | 3.3 | MAXIMUM VALUE | — | FIRST HEARTBEAT END |
| 9 | 1.5 | 6.7 | 3.3 | — | MINIMUM VALUE | SECOND HEARTBEAT START |
| 10 | 5.5 | 6.7 | 3.3 | — | — | 2 |
| 11 | 2.0 | 6.7 | 3.3 | — | MINIMUM VALUE | 2 |
| 12 | 8.5 | 6.7 | 3.3 | — | — | 2 |
| 13 | 10.0 | 6.7 | 3.3 | MAXIMUM VALUE | — | SECOND HEARTBEAT END |
| 14 | 1.5 | 6.7 | 3.3 | — | MINIMUM VALUE | THIRD HEARTBEAT START |
| 15 | 9.0 | 6.7 | 3.3 | — | — | 3 |
| 16 | 10.0 | 6.7 | 3.3 | MAXIMUM VALUE | — | 3 |
| 17 | 5.0 | 6.7 | 3.3 | — | — | 3 |
| 18 | 9.5 | 6.7 | 3.3 | MAXIMUM VALUE | — | 3 |
| 19 | 4.5 | 6.7 | 3.3 | — | — | THIRD HEARTBEAT END |
| 20 | 1.5 | 6.7 | 3.3 | — | MINIMUM VALUE | FOURTH HEARTBEAT START |

Fig. 15

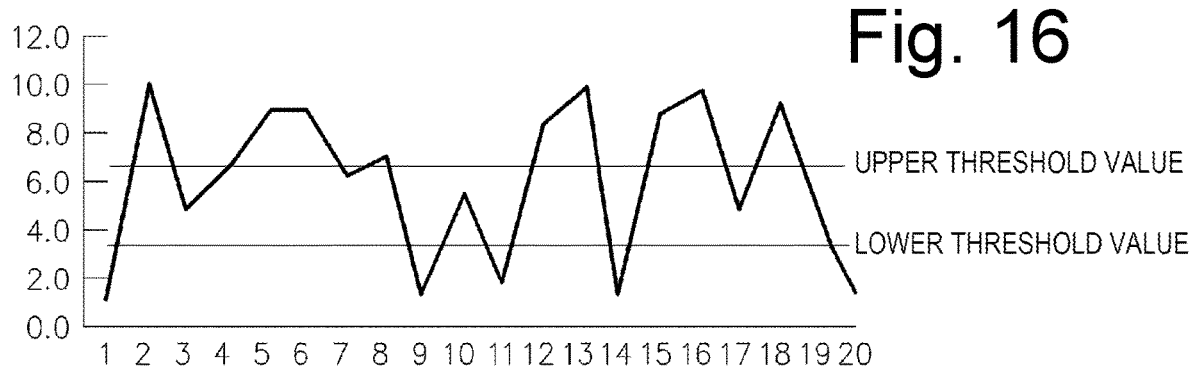

Fig. 16

EXTRACORPOREAL CIRCULATION MANAGEMENT DEVICE WITH HEARTBEAT SYNCHRONIZATON

CROSS REFERENCE TO RELATED APPLICATIONS

This application is a continuation of PCT Application No. PCT/JP2017/006778, filed Feb. 23, 2017, based on and claiming priority to Japanese Application No. 2016-054036, filed Mar. 17, 2016, both of which are incorporated herein by reference in their entirety.

BACKGROUND OF THE INVENTION

The present invention relates to an extracorporeal circulation management device, an extracorporeal circulator, an extracorporeal circulation management program, and a control method of an extracorporeal circulation management device, for example, which are used in order to manage extracorporeal circulation for supplying blood to a patient.

BACKGROUND ART

In the related art, for example, a method called "intra-aortic balloon pumping (IABP)" is known. According to the method, a balloon is located inside an aorta. The balloon is inflated during a diastolic phase of a heart, and conversely, the balloon is deflated during a systolic phase of the heart, thereby reducing a load on the heart. The IABP can be synchronized with heartbeats of the heart. However, there is a problem in that a cardiac sparing effect may be low. Furthermore, percutaneous cardiopulmonary support (PCPS) has been used as an extracorporeal circulation technique. According to this percutaneous cardiopulmonary support, cardiopulmonary support is generally performed via a femoral artery by using an artificial cardiopulmonary device (extracorporeal circulator) of a closed circuit using a centrifugal pump and a membrane type artificial lung. According to this extracorporeal circulator, a constant blood flow is continuously supplied to a patient. Accordingly, the cardiac sparing effect is higher than that of the IABP. However, the continuous (i.e., non-pulsating) blood flow from the pump collides with pulsating blood delivered from the heart of the patient. Consequently, there is a phenomenon called "mixing" in which an effect of the PCPS decreases. Moreover, there is a problem in that a cardiac afterload increases.

The problems can be mitigated using the two methods together and combining advantageous points of both methods with each other. However, another problem still remains in that devices are inconveniently used together in order to use the two methods and the devices have to be accurately synchronized with each other.

On the other hand, the following technique also has been proposed. An electromagnetic valve has been incorporated in the extracorporeal circulator so as to enable the blood to be supplied in accordance with the heartbeats of the patient (for example, U.S. application publication US2008/0249456A1).

However, in a case of this proposal, the electromagnetic valve is used, and the electromagnetic valve directly comes into contact with the blood. Consequently, there is a possibility that the blood may be damaged (injured).

SUMMARY OF THE INVENTION

Therefore, an object of the present invention is to provide an extracorporeal circulation management device, an extracorporeal circulator, an extracorporeal circulation management program, and a control method of an extracorporeal circulation management device, in which blood can be supplied in synchronization with heartbeats of a heart without using a plurality of devices and without causing damage to the blood.

According to the present invention, the above-described object is realized by an extracorporeal circulation management device including i) a flow rate information storage unit that stores information on the flow rate of the blood of a target person (patient), which is acquired from a flow rate measurement unit, ii) a candidate information generation unit that identifies systolic phase candidate information which may potentially correspond to systolic phase information on a systolic phase in which a heart of the target person contracts and diastolic phase candidate information which may potentially correspond to diastolic phase information on a diastolic phase in which the heart expands, based on information on comparison of a plurality of the flow rate information items acquired in time series, and iii) a systolic-diastolic phase information generation unit that identifies the systolic phase information and the diastolic phase information in each heartbeat, based on information on appearance of a plurality of the systolic phase candidate information items and a plurality of the diastolic phase candidate information items acquired in time series. Blood supply starting information (i.e., start command) for commencing blood supply or blood supply stop information (i.e., stop command) for stopping the blood supply is transmitted to a motor unit, based on the systolic phase information and the diastolic phase information.

According to a preferred embodiment, based on the information on comparison of a plurality of the flow rate information items (for example, the flow rate value is the "greatest" or "smallest"), for example, three items of the flow rate information acquired in time series, it is possible to identify the systolic phase candidate information (for example, a "minimum value") which may potentially correspond to the systolic phase information on the systolic phase in which a heart of a target person such as a patient contracts, and the diastolic phase candidate information (for example, a "maximum value") which may potentially correspond to the diastolic phase information on the diastolic phase in which the heart expands. Therefore, the systolic phase candidate information and the diastolic phase candidate information are extracted and identified from information on the flow rate of the actual blood flow of the patient (e.g., before operating the pump motor). In this manner, it is possible to accurately acquire timing candidate information relating to the heartbeats including a systolic phase and a diastolic phase of the heart of the patient.

In addition, according to a preferred embodiment, based on the information on appearance of a plurality of the systolic phase candidate information items and a plurality of the diastolic phase candidate information items which are acquired in time series, the systolic phase information and the diastolic phase information in each heartbeat are identified. Accordingly, it is possible to precisely eliminate noisy data which indicates wrong systolic phase candidate information and wrong diastolic phase candidate information. Based on the heartbeats of the heart of the patient, it is possible to precisely recognize the systolic phase information and the diastolic phase information.

Based on the systolic phase information and the diastolic phase information described above, a blood supply commencement information (i.e., circulation command) for commencing the blood supply or a blood supply stop information (i.e., stop command) for stopping the blood supply is transmitted to the motor unit. Accordingly, the blood can be supplied in synchronization with the heartbeats of the heart without using a plurality of devices and without causing damage to the blood.

Preferably, based on the comparison information and threshold value information (e.g., upper and lower thresholds) serving as reference information for the systolic phase information or the diastolic phase information, it is determined whether or not the flow rate information corresponds to the systolic phase candidate information or the diastolic phase candidate information.

According to a preferred embodiment, based on the comparison information and the threshold value information serving as the reference information for the systolic phase information or the diastolic phase information, it is determined whether or not the flow rate information (i.e., the maxima and minima) corresponds to the systolic phase candidate information or the diastolic phase candidate information. Accordingly, it is possible to precisely determine whether or not the flow rate information indicates the systolic phase candidate information or the diastolic phase candidate information.

Preferably, the comparison information is comparison information among three items of the flow rate information in time series.

According to a preferred embodiment, the comparison information is obtained from three consecutive items of the flow rate information which are acquired in time series. Accordingly, since the comparison information is used, it is possible to precisely recognize a change in the actual flow rate information.

Preferably, difference information among the systolic phase candidate information, the diastolic phase candidate information, and an actual heartbeat is acquired as difference change information, and based on the difference change information, the systolic phase information and the diastolic phase information are corrected.

According to a preferred embodiment, the difference information among the systolic phase candidate information, the diastolic phase candidate information, and the actual heartbeats is acquired as the difference change information (for example, difference value data). Based on the difference change information, the systolic phase information and the diastolic phase information are corrected. Accordingly, the pumped blood can always be supplied in synchronization with the heartbeats of the heart. In addition, the correction is performed, based on the difference change information. Accordingly, it is possible to easily perform the correction.

Preferably, the extracorporeal circulator has an artificial lung unit that performs gas exchange on blood of a target person, a tube unit that connects the artificial lung unit and a patient to each other, a flow measurement unit that measures a blood flow inside the tube unit, and a motor unit that supplies the blood flowing inside the tube unit.

Preferably, the extracorporeal circulator further has a blood supply period change information storage unit that stores blood supply period change information for changing a blood supply period of the artificial lung unit, based on a tube unit length which is a length of the tube unit between the artificial lung unit and the target person.

According to a preferred embodiment, the extracorporeal circulator further has the blood supply period change information storage unit that stores the blood supply period change information for changing the blood supply period of the artificial lung unit, based on the tube unit length (for example, a tube length) which is the length of the tube unit between the artificial lung unit and the target person. Therefore, even if the length of the tube unit such as the tube used by each extracorporeal circulator varies, the blood can always be supplied in synchronization with the heartbeats of the heart at optimal timing.

According to the present invention, the above-described object is realized by an extracorporeal circulation management program for causing an extracorporeal circulation management device to function as i) a flow rate information storage unit that stores information on the flow rate of blood of a target person, which is acquired from a flow rate measurement unit, ii) a candidate information generation unit that identifies systolic phase candidate information which may possibly correspond to systolic phase information on a systolic phase in which a heart of the target person contracts and diastolic phase candidate information which may possibly correspond to diastolic phase information on a diastolic phase in which the heart expands, based on information on comparison of a plurality of the flow rate information items acquired in time series, and iii) a systolic-diastolic phase information generation unit that identifies the systolic phase information and the diastolic phase information in each heartbeat, based on information on appearance of a plurality of the systolic phase candidate information items and a plurality of the diastolic phase candidate information items acquired in time series. The extracorporeal circulation management device is caused to function so that blood supply starting information (i.e., start command) for commencing blood supply or blood supply stop information (i.e., stop command) for stopping the blood supply is transmitted to a motor unit, based on the systolic phase information and the diastolic phase information.

According to the present invention, the above-described object is realized by a control method of an extracorporeal circulation management device. The control method includes i) storing information on the flow rate of blood of a target person, which is acquired from a flow rate measurement unit, in a flow rate information storage unit, ii) identifying systolic phase candidate information which may possibly correspond to systolic phase information on a systolic phase in which a heart of the target person contracts and diastolic phase candidate information which may possibly correspond to diastolic phase information on a diastolic phase in which the heart expands, based on information on comparison of a plurality of the flow rate information items acquired in time series, iii) identifying the systolic phase information and the diastolic phase information in each heartbeat, based on information on appearance of a plurality of the systolic phase candidate information items and a plurality of the diastolic phase candidate information items acquired in time series, and iv) transmitting blood supply information for blood supply or blood supply stop information for stopping the blood supply, to a motor unit, based on the systolic phase information and the diastolic phase information.

As described above, according to the present invention, there are advantageous effects as follows. It is possible to provide an extracorporeal circulation management device, an extracorporeal circulator, an extracorporeal circulation management program, and a control method of an extracorporeal circulation management device, in which blood can be supplied in synchronization with heartbeats of a heart without using a plurality of devices and without causing damage to the blood.

BRIEF DESCRIPTION OF THE DRAWINGS

FIG. 3 is a schematic block diagram illustrating a main configuration of a first various information storage unit.

FIG. 4 is a schematic block diagram illustrating a main configuration of a second various information storage unit.

FIG. 5 is a schematic block diagram illustrating a main configuration of a third various information storage unit.

FIG. 6 is a schematic block diagram illustrating a main configuration of a fourth various information storage unit.

FIG. 14 is a schematic view for describing an example of flow rate data stored in a flow rate data storage unit.

FIG. 15 is a schematic view for describing sample data of data of the "flow rate data storage unit" in FIG. 3.

FIG. 16 is another schematic view for describing sample data of data of the "flow rate data storage unit" in FIG. 3.

FIGS. 17A and 17B are schematic views for describing difference value data by using waveforms.

DETAILED DESCRIPTION OF PREFERRED EMBODIMENTS

Hereinafter, preferred embodiments according to the present invention will be described in detail with reference to the accompanying drawings. The embodiments described below are preferable specific examples according to the present invention. Therefore, the embodiments have various technically preferable limitations. However, the scope of the present invention is not limited to the aspects unless the present invention is particularly limited in the following description.

Figure 1:
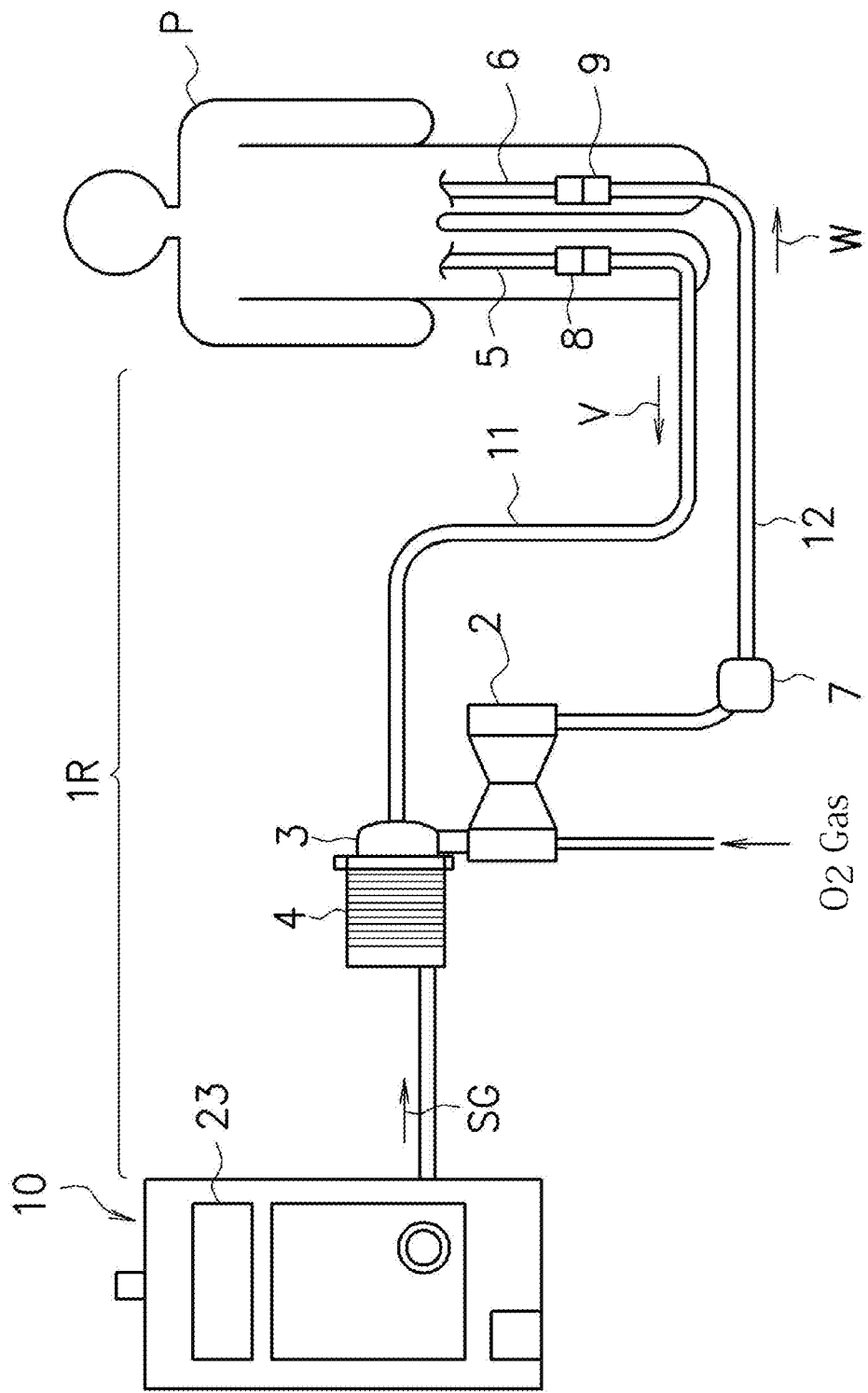
FIG. 1 is a schematic view illustrating a main configuration of an extracorporeal circulator according to an embodiment of the present invention.

FIG. 1 is a schematic view illustrating a main configuration of an extracorporeal circulator 1 according to an embodiment of the present invention. The extracorporeal circulator 1 illustrated in FIG. 1 performs extracorporeal circulation on blood of a patient P, for example, who is a target person illustrated in FIG. 1. When the extracorporeal circulator 1 is used, in some cases, it is considered that the heart of the patient P is not functioning normally, or the heart is functioning normally but the lung is not functioning normally.

Incidentally, the extracorporeal circulator 1 illustrated in FIG. 1 according to the present embodiment is used in a case where cardiac surgery is performed on the patient P or in a case of subsequent treatment in an intensive care unit (ICU).

Specifically, a "centrifugal pump 3" is operated via a drive motor 4, for example, which is a motor unit of the extracorporeal circulator 1 so as to remove the blood from a vein (vena cava) of the patient P. Gas exchange in the blood is performed using an artificial lung 2, for example, which is an artificial lung unit, and performs oxygenation of the blood. Thereafter, the extracorporeal circulator 1 performs "artificial lung extracorporeal blood circulation" for returning the blood again to an artery (aorta) of the patient P. That is, the extracorporeal circulator 1 functions as a substitution for the heart and the lung.

In addition, the extracorporeal circulator 1 adopts the following configuration. That is, as illustrated in FIG. 1, the extracorporeal circulator 1 has a "circulation circuit 1R" which circulates the blood. The circulation circuit 1R has the "artificial lung 2", the "centrifugal pump 3", the "drive motor 4", a "venous cannula (blood removal side cannula) 5, an "arterial cannula (blood supply side cannula) 6", and a controller 10, for example, which is an extracorporeal circulation management device. The centrifugal pump 3 is also called a blood pump, and pumps other than the centrifugal pump can also be used.

The venous cannula (blood removal side cannula) 5 in FIG. 1 is inserted via a connector 8 through the femoral vein, and a distal end of the venous cannula 5 is caused to indwell the right atrium. The arterial cannula (blood supply side cannula) 6 is inserted via a connector 9 in FIG. 1 through the femoral artery. The venous cannula 5 is connected to the centrifugal pump 3 via the connector 8 by using a blood removal tube 11, for example, which is the tube unit. The blood removal tube (also called a "blood removal line") 11 is a conduit line for supplying the blood.

A configuration is adopted as follows. If the drive motor 4 operates the centrifugal pump 3 by a command SG of the controller 10, the centrifugal pump 3 removes the blood from the blood removal tube 11, and causes the blood passing through the artificial lung 2 to return to the patient P via a blood supply tube 12 (also referred to as a "blood supply line"), for example, which is the tube unit.

The artificial lung 2 is located between the centrifugal pump 3 and the blood supply tube 12. The artificial lung 2 introduces oxygen gas as illustrated in FIG. 1, and performs a gas exchange operation (oxygen addition and/or carbon dioxide removal) on the blood. For example, the artificial lung 2 is a membrane type artificial lung. However, particularly preferably, a hollow fiber membrane type artificial lung is used. The blood supply tube 12 is a conduit line which connects the artificial lung 2 with the arterial cannula 6 to each other. For example, the blood removal tube 11 and the blood supply tube 12 are conduit lines made of synthetic resin which is highly transparent and flexible, such as vinyl chloride resin and silicone rubber. Inside the blood removal tube 11, the blood flows in a direction V, and inside the blood supply tube 12, the blood flows in a direction W.

In addition, in the extracorporeal circulator 1, as illustrated in FIG. 1, a flow rate sensor 7, for example, which is a flow rate measurement unit for measuring a flow rate value of the blood inside the blood supply tube 12, is located in the blood supply tube 12.

Incidentally, the controller 10 of the extracorporeal circulator 1 illustrated in FIG. 1 has a computer, and the computer has a central processing unit (CPU), a random access memory (RAM), and a ROM (Read Only Memory). These are connected to each other via a bus.

Figure 2:
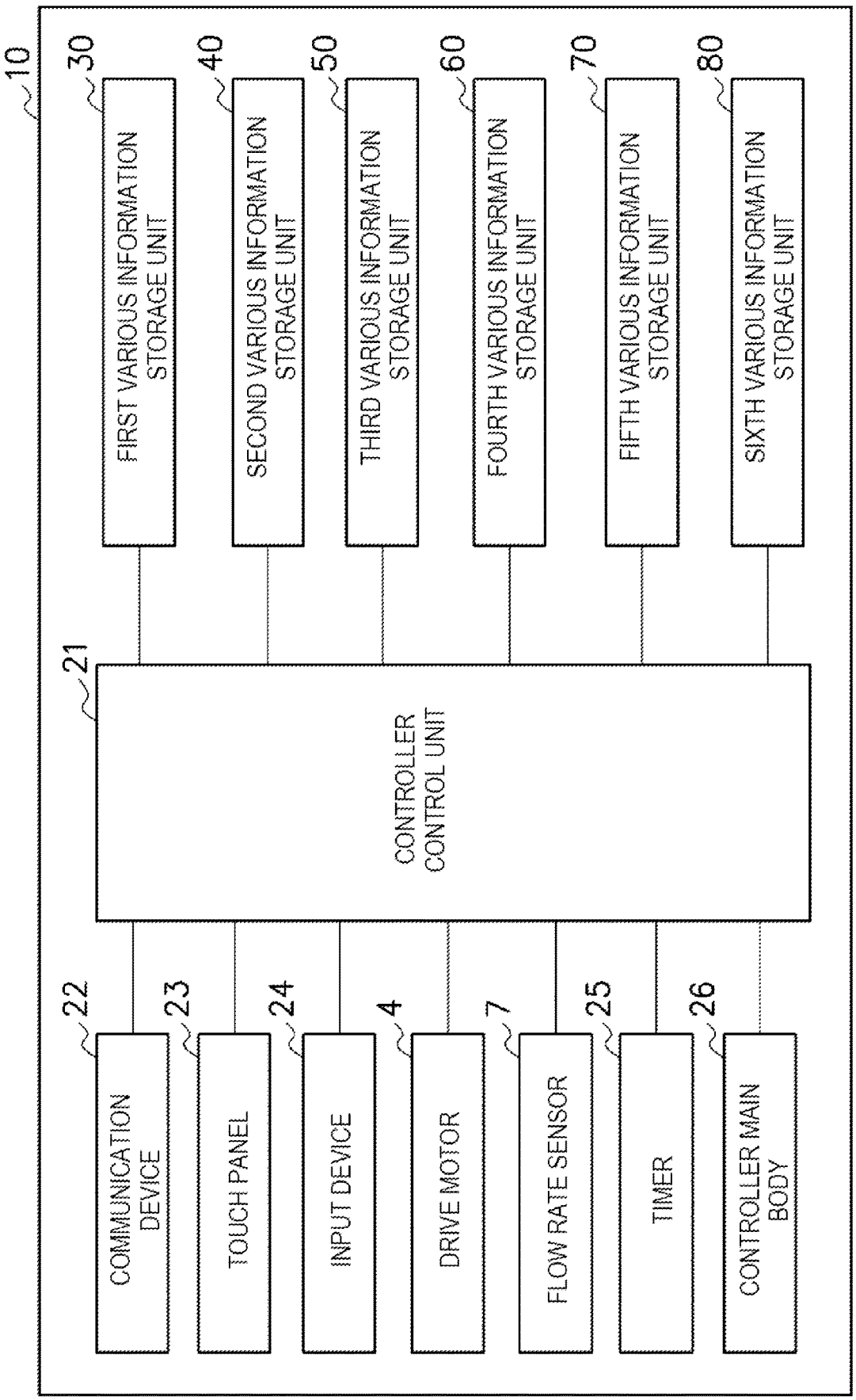
FIG. 2 is a schematic block diagram illustrating a main configuration of a controller of the extracorporeal circulator in FIG. 1.

FIG. 2 is a schematic block diagram illustrating a main configuration of the controller 10 of the extracorporeal circulator 1 in FIG. 1. As illustrated in FIG. 2, the controller 10 has a "controller control unit 21", and the controller control unit 21 is configured to be capable of controlling the drive motor 4 and the flow rate sensor 7 which are illustrated in FIG. 1, a communication device 22 for communicating with other devices, and a "touch panel 23" formed of color liquid crystal or organic EL, which displays various information items and to which various information items can be input. In addition, the controller 10 also controls an input device 24 for inputting various information items, a timer 25 for generating time information, and a controller main body 26.

Furthermore, the controller control unit 21 controls a "first various information storage unit 30", a "second various information storage unit 40", a "third various information storage unit 50", a fourth various information storage unit 60", a "fifth various information storage unit 70", and a "sixth various information storage unit 80" which are illustrated in FIG. 2. FIGS. 3 to 8 are respectively schematic block diagrams illustrating each main configuration of the "first various information storage unit 30", the "second various information storage unit 40", the "third various information storage unit 50", the "fourth various information storage unit 60", the "fifth various information storage unit 70", and the "sixth various information storage unit 80". These memory contents will be described later.

FIGS. 9 to 13 are schematic flowcharts illustrating a main operation example of the extracorporeal circulator 1 in FIG. 1. Hereinafter, description will be made with reference to these flowcharts, and the configurations in FIGS. 1 to 8 will be described. First, in a state where the extracorporeal circulator 1 in FIG. 1 is not operated, the venous cannula 5 and the arterial cannula 6 are respectively inserted into and located in the femoral vein and femoral artery of the patient P. In this state, the process proceeds to Step (hereinafter, referred to as "ST") 1.

The heart of the patient P contracts so as to push the blood inside the heart into the artery (systolic phase), and expands so as to receive the blood from the vein (diastolic phase) regularly. This operation is performed by the cardiac muscle (heart muscle) configuring the heart wall. This operation is called the heartbeat. An average heart rate for one minute is 62 to 72 in a case of adult males, and is 70 to 80 in a case of females. There is a tendency that elderly people have a lower rate and children have a higher rate.

Figure 9:
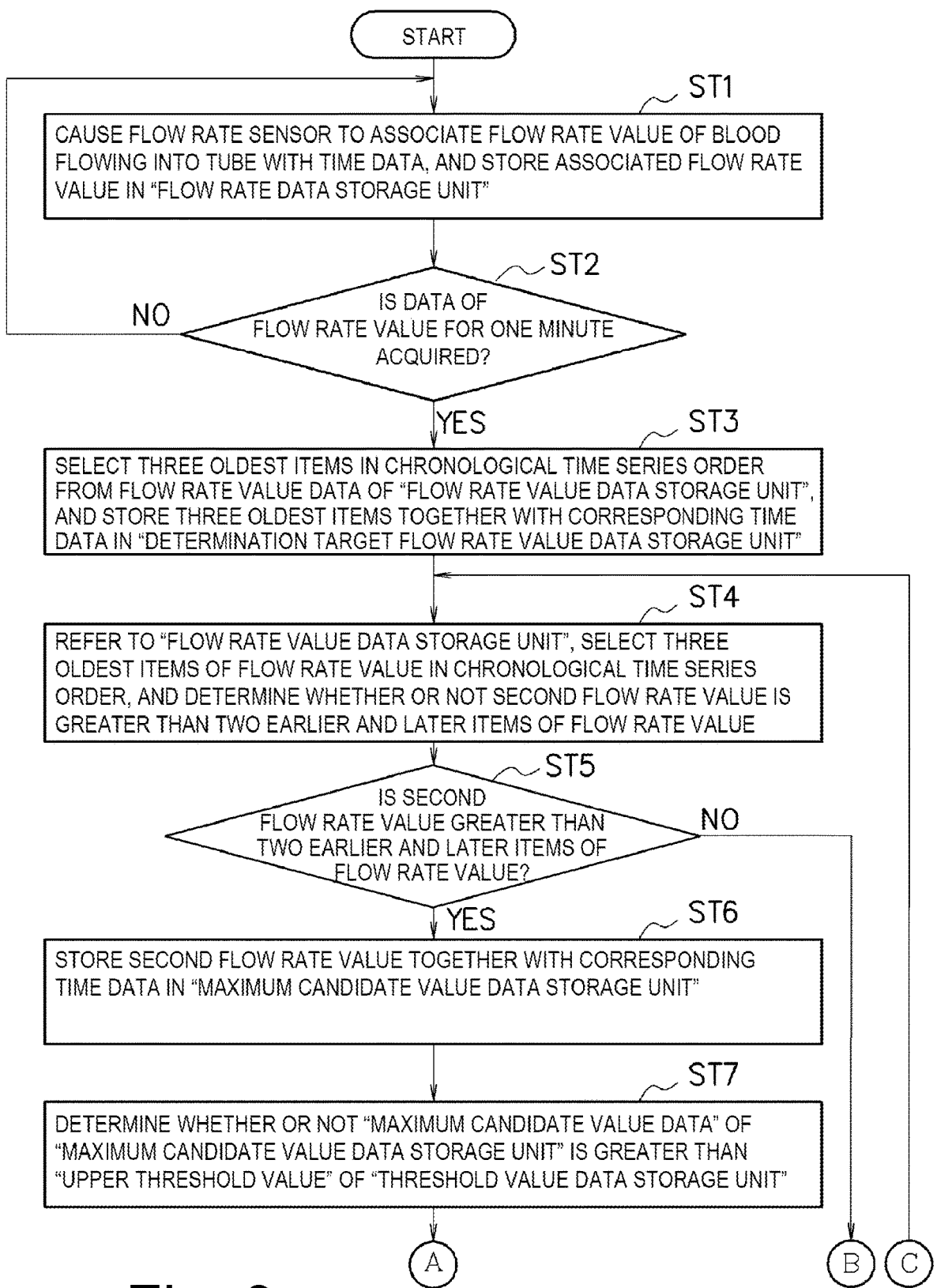
FIG. 9 is a schematic flowchart illustrating a main operation example of the extracorporeal circulator in FIG. 1.
Figure 10:
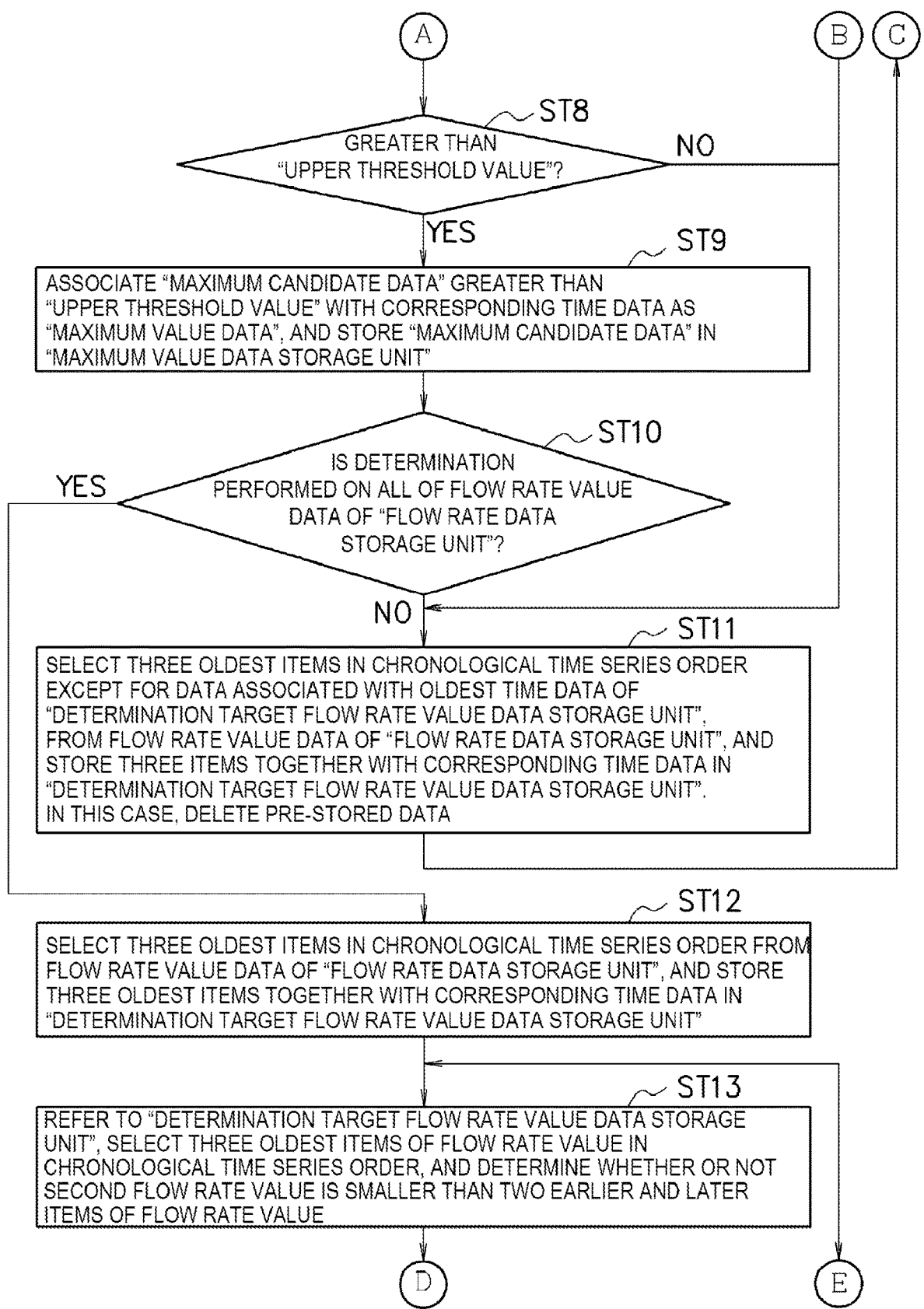
FIG. 10 is another schematic flowchart illustrating a main operation example of the extracorporeal circulator in FIG. 1.
Figure 11:
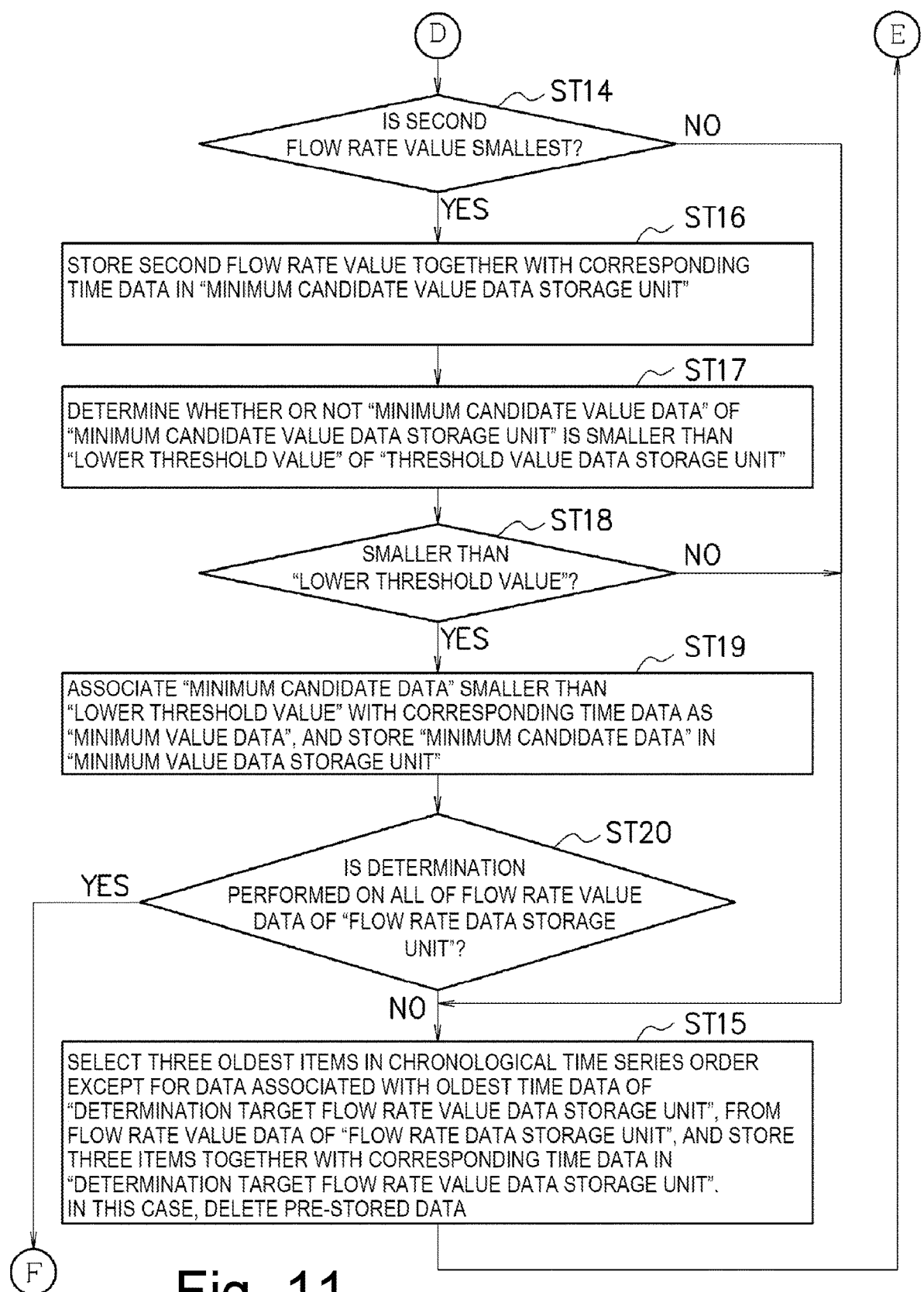
FIG. 11 is still another schematic flowchart illustrating a main operation example of the extracorporeal circulator in FIG. 1.
Figure 12:
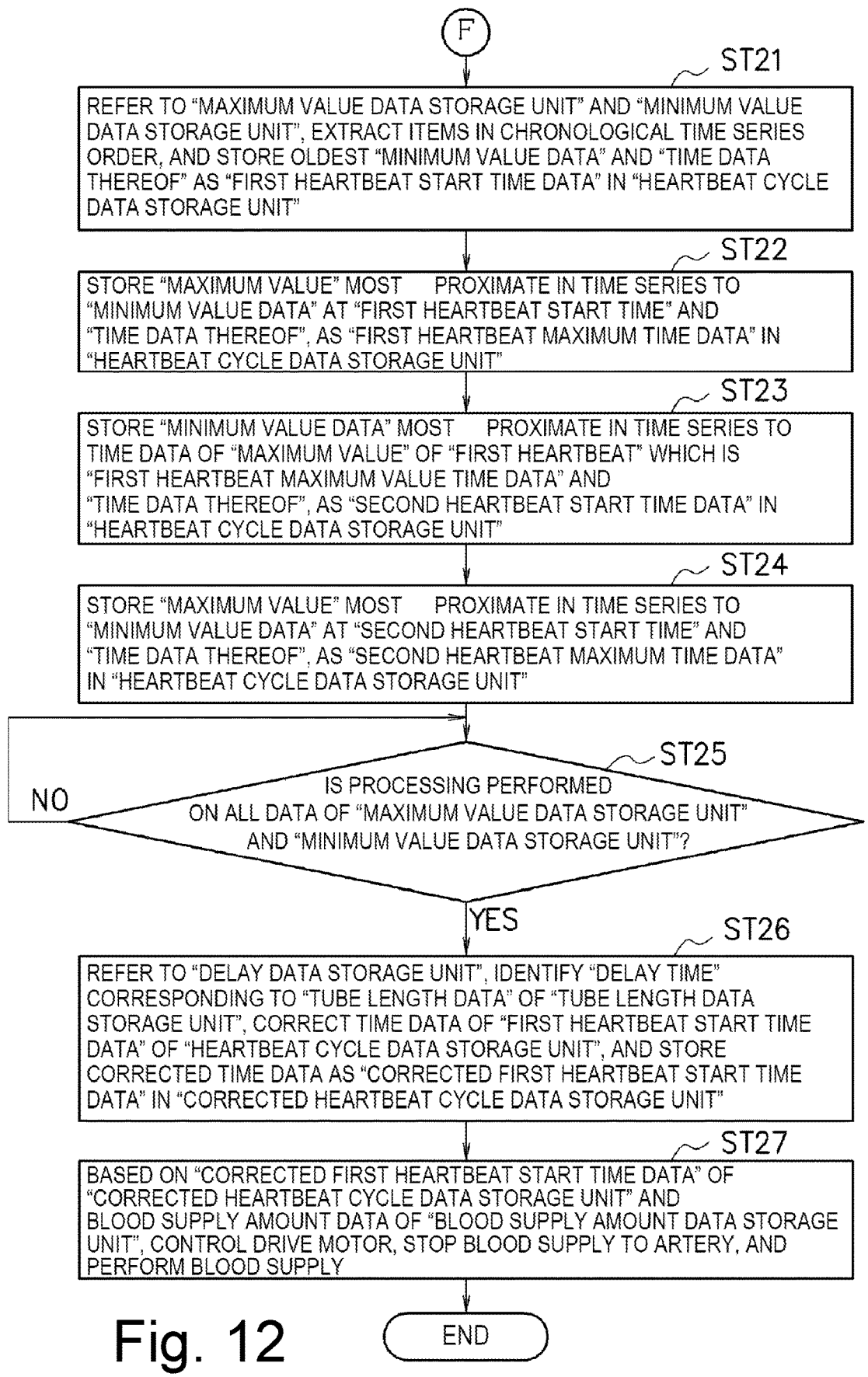
FIG. 12 is still another schematic flowchart illustrating a main operation example of the extracorporeal circulator in FIG. 1.

Therefore, in a state where the extracorporeal circulator 1 is connected to the patient P and the centrifugal pump 3 is not operated, the flow rate sensor 7 of the extracorporeal circulator 1 measures a change (i.e., pulsations) in the flow rate value of the blood caused by the heartbeats of the patient P. As illustrated in FIG. 9, in ST1, the flow rate sensor 7 measures the flow rate value (an example of flow rate information) of the blood of the patient P which flows in the blood supply tube 12, and associates (i.e., combines) the flow rate value with time data of the timer 25 in FIG. 2 so as to be stored in a "flow rate data storage unit 31", for example, which is a flow rate information storage unit in FIG. 3.

FIG. 14 is a schematic view for describing an example of flow rate data stored in the flow rate data storage unit 31. As illustrated in FIG. 14, the flow rate value reflects pulsatile changes caused by the heartbeat of the heart of the patient P.

Next, in ST2, it is determined whether or not the data of the flow rate value for one minute has been acquired. When the data of the flow rate value for one minute is acquired, the process proceeds to ST3. In ST3, a "first determination target flow rate value data extraction processing unit (program) 32" in FIG. 3 is operated, and three oldest items of the flow rate value data of the "flow rate data storage unit 31" are selected in chronological time series order. The three items together with corresponding time data are stored in a "determination target flow rate value data storage unit 33" in FIG. 3.

FIGS. 15 and 16 are schematic views for describing sample data of the data of the "flow rate data storage unit 31" in FIG. 3. In FIGS. 15 and 16, "1" to "20" indicate the time data (i.e., time slots) acquired in time series, and a sample value indicates the flow rate value at that time.

Then, according to the present embodiment, for example, time slots "1" to "3" (these are denoted as "X1" to "X3") are selected in chronological time series order for consideration as potential candidates for defining a particular phase (e.g. systolic phase) within a heartbeat cycle. A sampled flow rate value "1.0" occurs at time X1, a flow rate value "10.0" occurs at time X2, and a flow rate value "5.0" occurs at time X3. These flow rate values are associated with the time data (X1 and the like), and are stored in the "determination target flow rate value data storage unit 33".

Next, the process proceeds to ST4. In ST4, a "maximum candidate value data determination processing unit (program) 34" in FIG. 3 is operated so as to access the "flow rate data storage unit 31" in FIG. 3. Three oldest items in chronological time series order, in the above-described example, the respective flow rate values "1.0", "10.0", and "5.0" at X1, X2, and X3 are selected so as to determine whether or not the flow rate value at X2, for example, which is the second flow rate value is greater than the two earlier and later flow rate values (for example, X1 and X3).

According to the present embodiment, the second flow rate value "10.0" at X2 is greater than "1.0" at X1 and "5.0" at X3. Accordingly, in ST5, it is determined that "the second flow rate value is greatest", and the process proceeds to ST6. This term of "whether or not the second flow rate value is greatest" is an example of the comparison information.

In ST6, the second flow rate value "10.0" (for example, X2) together with the corresponding time data "X2" is stored in a "maximum candidate value data storage unit 35" in FIG. 3.

In this way, according to the present embodiment, a plurality of the flow rate values proximate to each other in time series, for example, three flow rate values are compared with each other. Accordingly, a change in the actual flow rate value can be precisely recognized.

Next, the process proceeds to ST7. In ST7, a "maximum value data determination processing unit (program) 36" in FIG. 3 is operated so as to determine whether or not the "maximum candidate value data" of the "maximum candidate value data storage unit 35", in the above-described example, the flow rate value "10.0" of the time data "X2" is greater than an "upper threshold value", for example, which is threshold value information of a "threshold value data storage unit 37".

That is, the "threshold value data storage unit 37" stores minimum reference information in a case where the flow rate value corresponds to the "systolic phase" or the "diastolic phase" of the above-described patient P. Specifically, if the flow rate value corresponds to the "diastolic phase", as illustrated in FIG. 15, "6.7" or greater is used as a reference, and is stored as "upper threshold value data". On the other hand, if the flow rate value corresponds to the "systolic phase", as illustrated in FIG. 15, "3.3" or smaller is used as the reference, and is stored as "lower threshold value data".

That is, even in a case of the "maximum candidate value data" in FIG. 3, if the flow rate value is not "equal to or greater than the upper threshold value", it is determined in this step that the flow rate value is not the flow rate value of the "diastolic phase". Therefore, the "diastolic phase" can be precisely determined.

In ST8, when it is determined in ST8 that the "maximum candidate value data" in FIG. 3 is the "upper threshold value (6.7) or greater", the process proceeds to ST9. In ST9, "maximum candidate data (for example, X2 (10.0))" greater than the "upper threshold value (6.7)" is associated with the corresponding time data (X2) as the maximum value data, and is stored in a "maximum value storage unit 41" in FIG. 4.

That is, the "maximum value data" is stored as influential data indicating the flow rate value of the "diastolic phase" of the patient P. This stored maximum value data is an example of "diastolic phase candidate information". In addition, the "maximum value data determination processing unit (program) 36" is an example of the candidate information generation unit.

Next, the process proceeds to ST10. In ST10, it is determined whether or not the flow rate value data of the "flow rate data storage unit 31" in FIG. 3, for example, all data for one minute are determined, and when it is determined that all data are not yet determined, the process proceeds to ST11.

In ST11, a "second determination target flow rate value data extraction processing unit (program) 42" in FIG. 4 is operated. From the flow rate value data of the "flow rate data storage unit 31" in FIG. 3, the data of the "determination target flow rate value data storage unit 33" in FIG. 3, in the above-described example, the oldest time data of X1 (1.0), X2 (10.0), X3 (5.0), except for the data (X1 (1.0)) associated with X1, in the above-described example, three oldest items of X2 (10.0), X3 (5.0), and X4 (6.5) in chronological time series order are selected.

Then, the selected data together with the corresponding time data is stored in the "determination target flow rate value data storage unit 33" in FIG. 3. In this case, pre-stored data, in the above-described example, X1 (1.0), X2 (10.0), and X3 (5.0) are deleted.

Next, in ST4, similar to the above-described step, it is determined whether or not the second flow rate value X3 (5.0) in this case is greater than the first flow rate value X2 (10.0) and the third flow rate value X4 (6.5). In a case where the second flow rate value is greater, the second flow rate value is compared with the "upper threshold value". If the second flow rate value is "equal to or greater than the upper threshold value", the second flow rate value is stored in the "maximum value storage unit 41". In this step, all data of the "flow rate data storage unit 31" are determined.

Then, according to the present embodiment, as illustrated in FIG. 15, for example, the time data items X2 (10.0), X8 (7.0), X13 (10.0), X16 (10.0), X18 (9.5) as the "maximum values", that is, as the flow rate value candidates of the "diastolic phase" of the heart of the patient P, are stored in the "maximum value data storage unit 41" in FIG. 4.

In ST10, if all of the flow rate value data for one minute in the "flow rate data storage unit 31" are completely determined, the process proceeds to ST12. In steps subsequent to ST12, it is determined whether the flow rate value data of the "flow rate data storage unit 31" may possibly correspond to correspond to the "systolic phase" of the heart of the patient P.

In ST11, the "first determination target flow rate value data extraction processing unit (program) 32" in FIG. 3 is operated. Similar to ST3, three oldest items in chronological time series order, for example, "1.0", "10.0", and "5.0" are selected from the flow rate value data of the "flow rate data storage unit 31" in FIG. 3, and are stored together with the corresponding time data items X1, X2, and X3 in the "determination target flow rate value data storage unit 33" in FIG. 3.

Next, the process proceeds to ST13. In ST13, a "minimum candidate value data determination processing unit (program) 43" in FIG. 4 is operated so as to refer to the "determination target flow rate value data storage unit 33". The flow rate value (1.0, 10.0, 5.0) of the three oldest items (for example, X1, X2, X3) in chronological time series order are selected so as to determine whether or not the second flow rate value, for example, the flow rate value at X2 "10.0" is smaller than two earlier and later flow rate values (for example, X1 and X3).

Next, in ST14, it is determined "whether or not the second flow rate value (X2 (10.0)) is smallest". However, in the above-described example, the second flow rate value is not smallest. Thus, the process proceeds to ST15. In ST15, similar to ST11 described above, the "second determination target flow rate value data extraction processing unit (program) 42" in FIG. 4 is operated. From the flow rate value data of the "flow rate data storage unit 31", except for the data of the "determination target flow rate value data storage unit 33" in FIG. 3, except for the data (for example, X1) associated with the oldest time data of X1, X2, and X3, three oldest items (for example, "10.0", "5.0", and "6.5") in chronological time series order are selected. The selected oldest items together with the corresponding time data (X2, X3, and X4) are stored in the determination target flow rate value data storage unit 33". In this case, pre-stored data is deleted.

Next, the process proceeds to ST13. In ST13, as described above, the "minimum candidate value data determination processing unit (program) 43" in FIG. 4 is operated so as to access the "determination target flow rate value data storage unit 33". The flow rate values ("10.0", "5.0", and "6.0") of the three oldest items (for example, X2, X3 and X4) in chronological time series order are selected so as to determine whether or not the second flow rate value for example, X3 "5.0" is smaller than the two earlier and later flow rate values (for example, X2 and X4).

Next, the process proceeds to ST14. In the above-described example, since the second flow rate value (X3 (5.0)) is smallest, the process proceeds to ST16. In ST16, the second flow rate value (for example, "5.0") together with the corresponding time data (X3) is stored in the "minimum candidate value data storage unit 44" in FIG. 4.

Next, in ST17, the "minimum value data determination processing unit (program) 45" in FIG. 4 is operated so as to determine whether or not the "minimum candidate value data" of the "minimum candidate value data storage unit 44" in FIG. 4, X3 (5.0) in the above-described example is smaller than the "lower threshold value" of the "threshold value data storage unit 37" in FIG. 3, for example, "3.3".

In the above-described example, X3 (5.0) is not smaller than the "lower threshold value (3.3)". Accordingly, it is determined that X3 (5.0) does not correspond to the "systolic phase" of the patient P, and the process proceeds to ST15. It is determined whether the second flow rate value is smallest among subsequent three items X3, X4, and X5, and it is further determined whether the second flow rate value is smaller than the "lower threshold value (3.3)".

In the example of FIG. 15, in a case where the three selected items are X8 (7.0), X9 (1.5), and X10 (5.5), the second flow rate value (X9 (1.5)) is smallest, and is smaller than the "lower threshold value (3.3)". Therefore, in this example, it is determined in ST18 that the second flow rate value is smaller than the "lower threshold value", and the process proceeds to ST19. In ST19, the "minimum candidate data (for example, X9 (1.5))" smaller than the "lower threshold value" is associated with the corresponding time data (X9) as the "minimum value data", and is stored in the "minimum value data storage unit 46" in FIG. 4.

This stored minimum value data is an example of the "systolic phase candidate information". In addition, the "minimum value data determination processing unit (program) 45" is an example of the candidate information generation unit.

Next, the process proceeds to ST20. In ST20, if all of the flow rate value data for one minute of the "flow rate data storage unit 31" are completely determined, the data is completely stored in the "minimum value storage unit 46". In the example of FIG. 15, for example, the time data items X1 (1.0), X9 (1.5), X11 (2.0), X14 (1.5), and X20 (1.5) as the "minimum values", that is, the flow rate value candidates of the "systolic phase" of the heart of the patient P, are stored in the "minimum value data storage unit 46" in FIG. 4.

Next, the process proceeds to ST21. In ST21, the data stored in the "maximum value data storage unit 41" and the "minimum value data storage unit 46" in FIG. 4 may possibly include not only the data corresponding to the "systolic phase" and the "diastolic phase" of the patient P but also noise data. Accordingly, the noise data is deleted in the following step.

That is, a "heartbeat noise deletion processing unit (program) 51" in FIG. 5 is operated so as to access the "maximum value data storage unit 41" and the "minimum value data storage unit 46" in FIG. 3, and oldest items in chronological time series order are extracted. In the example of FIG. 15, X1 (minimum value), X2 (maximum value), X8 (maximum value), X9 (minimum value), X11 (minimum value), X13 (maximum value), X14 (minimum value), X16 (maximum value), X18 (maximum value), and X20 (minimum value) are the oldest items in chronological order.

Then, the oldest "minimum value data" "1.0" and "time data thereof" "X1" are set as "first heartbeat start time data" at a "start time" of a "first heartbeat", and are stored in a "heartbeat cycle data storage unit 52" in FIG. 5. This "first heartbeat start time data" is an example of the systolic phase information.

Next, the process proceeds to ST22. In ST22, the "maximum value" and "time data thereof" which are most proximate in time series to "X1" in FIG. 15 which is "minimum value data" corresponding to a "first heartbeat start time", in the example of FIG. 15, "X2" as the maximum value of the "first heartbeat" and "first heartbeat maximum time data" serving as time data thereof is stored in the "heartbeat cycle data storage unit 52" in FIG. 5. This "first heartbeat maximum time data" is an example of the diastolic phase information. In addition, the "heartbeat noise deletion processing unit (program) 51" is an example of the systolic-diastolic phase information generation unit.

Next, the process proceeds to ST23. In ST23, the time data of the "the maximum value" of the "first heartbeat" which is the "first heartbeat maximum value time data", in the above-described example, the "minimum value data" and "time data thereof" which are most proximate in time series to "X2", in the example of FIG. 15, as "second heartbeat start time data" at a "start time" of a "second heartbeat", "X9" is stored in the "heartbeat cycle data storage unit 52" in FIG. 5.

Therefore, the maximum value of "X8" in FIG. 15 is deleted as the noise data. The reason is as follows. The "minimum value" and the "maximum value" of the heartbeat alternately occur. Accordingly, "X8" which occurs continuously with "X2" is processed as the noise so as to precisely identify the "systolic phase" and the "diastolic phase" of the patient P.

Next, the "maximum value" and "time data thereof" most proximate in time series to "X9" in FIG. 15 which is the "minimum value data" corresponding to the "second heartbeat start time", in the example of FIG. 15, as the maximum value of the "second heartbeat" and the "second heartbeat maximum time data" serving as the time data, "X13" is stored in the "heartbeat cycle data storage unit 52". That is, the "minimum value" of X11 is deleted as the noise.

This determination is continued so as to determine all data of the "maximum value data storage unit 41" and the "minimum value data storage unit 46". In ST 25, when all data are completely processed, with regard to the flow rate data for one minute of the "flow rate data storage unit 31", the information on the heartbeats having the "systolic phase" and the "diastolic phase" of the patient P is stored in the "heartbeat cycle data storage unit 52" in FIG. 5. For example, the data of the "systolic phase (heartbeat start time)" and the "diastolic phase (heartbeat maximum time)" of the respective heartbeats repeated 120 times per minute are stored together with the time information.

Next, the process proceeds to ST26. As illustrated in FIG. 1, the extracorporeal circulator 1 supplies the blood from the artificial lung 2 to the patient P via the blood supply tube 12. Then, in this case, the blood is supplied by synchronizing timings of the "systolic phase" and the "diastolic phase" of the heart of the patient P with each other.

However, the length of the blood supply tube 12 of the extracorporeal circulator 1 may vary depending on a type of the extracorporeal circulator 1 in some cases. Accordingly, in view of the length of the blood supply tube 12, the blood supply from the artificial lung 2 to the patient P has to be synchronized for each of the "systolic phase" and the "diastolic phase" of the heart of the patient P in a manner that compensates for the time delay associated with the flow traversing the supply tube 12. Therefore, according to the present embodiment, in accordance with the length of the tube unit length of the extracorporeal circulator 1, for example, the length of the blood supply tube 12, timings are adjusted so as to synchronize the expansion and contraction of the heart in the patient P with the blood supply.

First, in ST26, a "corrected heartbeat cycle data generation processing unit (program) 61" in FIG. 6 is operated so as to access a blood supply period change time storage unit in FIG. 5, for example, a "delay data storage unit 53".

The "delay data storage unit 53" stores a delay time (ΔT1) corresponding to the length of the blood supply tube 12. That is, depending on the length of the blood supply tube 12 between the artificial lung 2 and the patient P, an arrival timing of the "blood" supplied from the artificial lung 2 to the patient P varies. Therefore, data of an arrival delay time of the "blood" is stored in accordance with the length of the blood supply tube 12 to be located in advance.

For example, a computation expression is as follows:

$$\Delta T_1 = \frac{L}{V}$$

where $\Delta T_1$ is the delay time, L is the tube length, and V is the flow velocity average of blood flowing in the motor. Moreover, V (flow velocity average of blood flowing in the motor) is equal to Q/A, where Q is an assumed flow rate and A is a cross-sectional area of the tube. For example, in a case of L=1.5 m and V=0.94 m/sec (Q=4.0 L/min, and tube diameter=approximately 9.5 mm), then ΔT1 is approximately 1.6 seconds.

Therefore, in this step, the "delay time" corresponding to the "length data of the blood supply tube 12" stored in a "tube length data storage unit 54" in FIG. 5 is identified. The time data items such as "first heartbeat start time data", "first heartbeat maximum time data", "second heartbeat start time data", and "second heartbeat maximum time data" of the "heartbeat cycle data storage unit 52" in FIG. 5 are corrected. The time data items are stored as "corrected first heartbeat start time data", "corrected first heartbeat maximum time data", "corrected second heartbeat start time data", and "corrected second heartbeat maximum time data" in a "corrected heartbeat cycle data storage unit 62" in FIG. 6.

In this manner, the "corrected first heartbeat start time data" and the "corrected first heartbeat maximum time data" which are stored in the "corrected heartbeat cycle data storage unit 62" can synchronize the "systolic phase" and the "diastolic phase" of the heart of the patient P with the blood supply to the patient P at an optimum timing adjusted in view of the length of the blood supply tube 12.

Next, the process proceeds to ST27. In ST27, a "blood supply operation instruction processing unit (program) 63" in FIG. 6 is operated. Based on the "corrected first heartbeat start time data", the "corrected first heartbeat maximum time data", the "corrected second heartbeat start time data", and the "corrected second heartbeat maximum time data" of the "corrected heartbeat cycle data storage unit 62" in FIG. 6, and the blood supply amount data {blood supply amount data from the artificial lung 2 (centrifugal pump 3) of the extracorporeal circulator 1 to the patient P} of the "blood supply amount data storage unit 64" in FIG. 6, the drive motor is controlled so as to stop the blood supply to the artery (aorta) during the systolic phase and to supply a predetermined amount of the blood during the diastolic phase. For example, at the time (timing) of the "corrected first heartbeat start time data", the blood supply is stopped, and at the time of the "corrected first heartbeat maximum time data", the blood is supplied.

This means that the timing of stopping the blood supply to the artery is the timing (systolic phase of the heart) at which the blood is ejected from the heart. In the systolic phase of the heart, the blood is delivered. Accordingly, the flow rate value of the flow rate sensor 7 is in a relationship where the flow rate value decreases against the pressure of the blood supply from the heart.

On the other hand, the timing of supplying the blood to the arteries is the timing (diastolic phase of the heart) at which the heart reserves the blood. In the diastolic phase of the heart, no blood is supplied from the heart, and thus, there is less resistance. Accordingly, the flow rate value of the flow rate sensor 7 is in a relationship where the flow rate value increases.

Therefore, based on the corrected heartbeat data for one minute (the "corrected first heartbeat start time data", the "corrected first heartbeat maximum time data", the "corrected second heartbeat start time data", and the "corrected second heartbeat maximum time data"), the blood supply is stopped during the corresponding phase, and the blood is supplied during the corresponding phase. In this manner, the blood can be supplied in synchronization with the heartbeats of the heart of the patient P. In this case, for example, the drive motor 4 generates the heartbeat 120 times for one minute in accordance with the heartbeats of the heart of the patient P.

In this way, according to the present embodiment, the blood can be supplied in synchronization with the heartbeats of the heart of the patient P by using only the extracorporeal circulator 1, without using a plurality of devices and without causing damage to the blood.

Incidentally, the IABP which has been used in the related art can be synchronized with the heart. However, the cardiac sparing effect is low. On the other hand, the PCPS has the higher cardiac sparing effect than that of the IABP. However, there is a phenomenon called "mixing" in which the effect of the PCPS decreases. Moreover, there is a problem in that a cardiac afterload increases. In this regard, according to the present embodiment, the blood is supplied to the patient in synchronization with the heartbeats of the heart of the patient P. Accordingly, it is possible to prevent the occurrence of mixing in which an effect decreases due to the blood flow colliding with blood delivered from the heart, and it is possible to prevent the occurrence of the cardiac afterload. Furthermore, since the IABP is not used, it is possible to prevent the inconvenience of synchronizing a plurality of devices with each other and the occurrence of a negative effect caused by a plurality of the devices.

In this way, according to the present embodiment, the blood can be supplied from the artificial lung 2 in synchronization with the heartbeats of the heart of the patient P. However, during the process of the blood supply, the blood supply may not be synchronized with the heartbeats of the heart of the patient P, in some cases. Therefore, according to the present embodiment, a correction step of the synchronization is performed as follows.

First, in ST31, the flow rate value of the flow rate sensor 7 in FIG. 2 is monitored, and the flow rate value together with the time data is stored in the "flow rate data storage unit 31" in FIG. 3.

Figure 7:
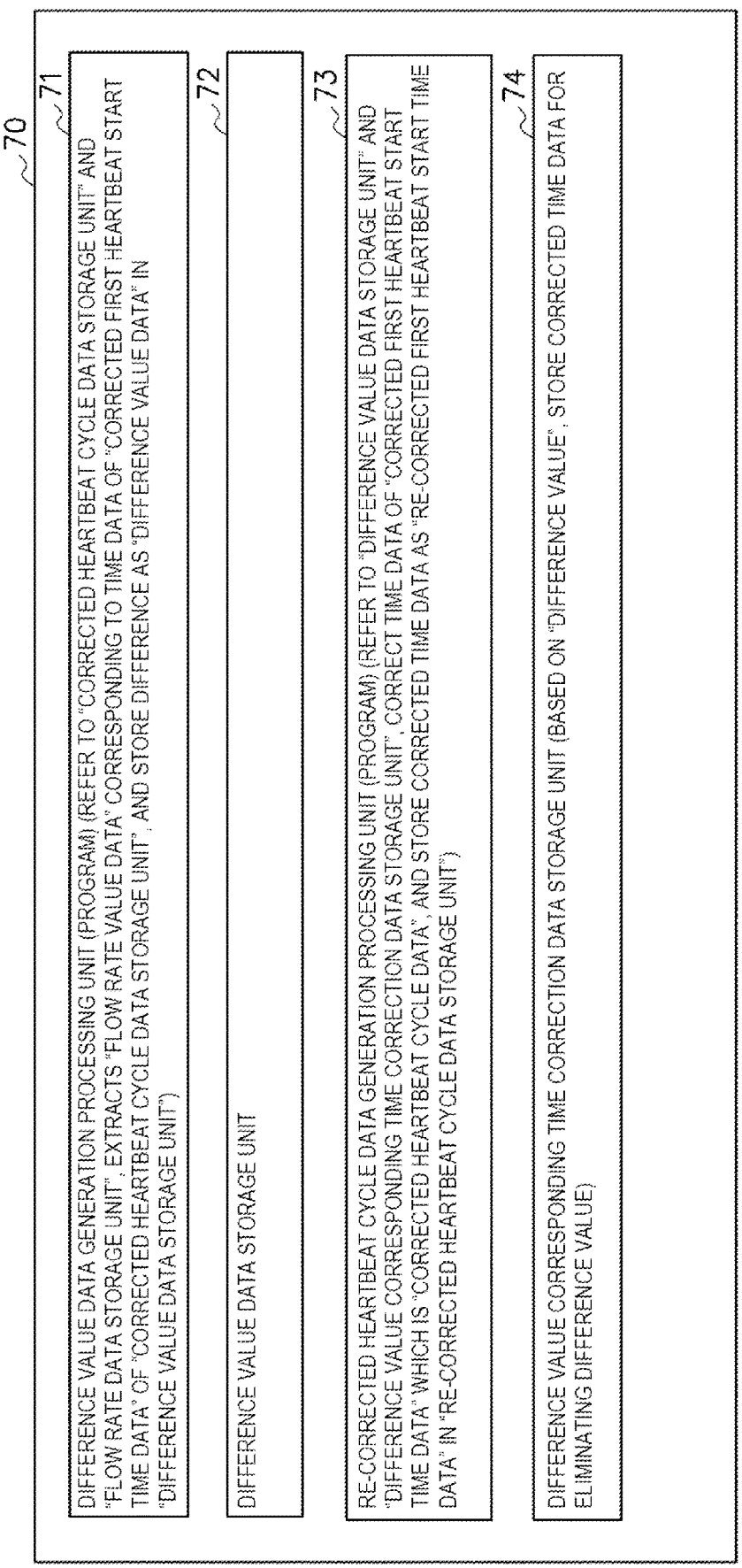
FIG. 7 is a schematic block diagram illustrating a main configuration of a fifth various information storage unit.

Next, the process proceeds to ST32. In ST32, a "difference value data generation processing unit (program) 71" in FIG. 7 is operated so as to access the "corrected heartbeat cycle data storage unit 62" in FIG. 6 and the "flow rate data storage unit 31" in FIG. 3. The "flow rate value data items" corresponding to the time data items such as the "corrected first heartbeat start time data", the "corrected first heartbeat maximum time data", the "corrected second heartbeat start time data", and the "corrected second heartbeat maximum time data" of the "corrected heartbeat cycle data storage unit 62" in FIG. 6 are extracted. A difference as "difference value data" is stored in a "difference value data storage unit 72" in FIG. 7. This "difference value data" is an example of the "difference change information".

FIGS. 17A and 17B are schematic views for describing the difference value data by using waveforms. FIG. 17A is a schematic view for describing the waveforms in a case where the time data such as the "corrected first heartbeat start time data", the "corrected first heartbeat maximum time data", the "corrected second heartbeat start time data", and the "corrected second heartbeat maximum time data" of the "corrected heartbeat cycle data storage unit 62" coincides with the time data of the heartbeat (the "systolic phase" and the "diastolic phase") of the heart of the patient P, that is, in a case where the timing of the controller 20 to turn on the supply of blood and to stop the blood supply to the patient P coincides with the heartbeat timing of the heart of the patient P.

In this case, as illustrated in FIG. 17A, for example, a flow rate value (h5) of the "flow rate sensor 7" at the same time data (timing) as a flow rate value (h1) of the "corrected first heartbeat maximum time data" controlled by the controller 10 is a sum of the flow rate value (h1) controlled by the controller 10 and a flow rate value (h2) inside the tube in the "diastolic phase" of the heart of the patient P, as illustrated in FIG. 1A. Difference value data thereof is the flow rate value (h2) inside the tube in the "diastolic phase" of the heart of the patient P.

On the other hand, a flow rate value (h6) of the "flow rate sensor 7" at the same time data (timing) as a flow rate value (h3) of the "corrected second heartbeat start time data" is a sum of the flow rate value (h3) controlled by the controller 10 and a flow rate value (h4) inside the tube in the "systolic phase" of the heart of the patient P, as illustrated in FIG. 17A. Difference value data thereof is the flow rate value (h4) inside the tube in the "systolic phase" of the heart of the patient P. Therefore, in FIG. 17A, the waveform of the flow rate value of the flow rate sensor 7 draws a large wave.

In contrast, FIG. 17B is a schematic view for describing the waveforms in a case where the time data such as the "corrected first heartbeat start time data", the "corrected first heartbeat maximum time data", the "corrected second heartbeat start time data", and the "corrected second heartbeat maximum time data" of the "corrected heartbeat cycle data storage unit 62" does not coincide with the time data of the heartbeat (the "systolic phase" and the "diastolic phase") of the heart of the patient P, that is, in a case where the timing of the controller 20 to turn on the supply of blood and to stop the blood supply to the patient P does not coincide with the heartbeat timing of the heart of the patient P.

In this case, as illustrated in FIG. 17B, for example, a flow rate value (h8) of the "flow rate sensor 7" at the same time data (timing) as the flow rate value (h1) of the "corrected first heartbeat maximum time data" controlled by the controller 10 is a sum of the flow rate value (h1) controlled by the controller 10 and a flow rate value (h7) inside the tube in the "systolic phase" of the heart of the patient P, as illustrated in FIG. 17B. Difference value data thereof is the flow rate value (h7) inside the tube in the "systolic phase" of the heart of the patient P.

On the other hand, a flow rate value (h11) of the "flow rate sensor 7" at the same time data (timing) as the flow rate value (h3) of the "corrected second heartbeat maximum time data" is a sum of the flow rate value (h3) controlled by the controller 10 and a flow rate value (h10) inside the tube in the "diastolic phase" of the heart of the patient P, as illustrated in FIG. 17B. Difference value data thereof is the flow rate value (h10) inside the tube in the "diastolic phase" of the heart of the patient P.

In this way, in a case of FIG. 17B, as illustrated, the heart of the patient P is in the "systolic phase" at the time data (timing) of the" corrected first heartbeat maximum time data" of the controller 10. Accordingly, the extracorporeal circulator 1 supplies the blood to the patient P, simultaneously with the "systolic phase" in which the heart delivers the blood. Consequently, the blood delivered from the extracorporeal circulator 1 and the blood delivered from the heart collide with each other, thereby causing a possibility of the "mixing". Consequently, the waveform of the flow rate value of the flow rate sensor 7 is substantially linear.

In this way, according to the present embodiment, the occurrence of the "mixing" in which the timing of supplying the blood and stopping the blood supply from the controller 10 and the timing of the heartbeat (the "systolic phase" and the "diastolic phase") of the heart of the patient P do not coincide with each other can be easily recognized using a difference between phases of the waveforms as illustrated in FIGS. 17A and 17B. Therefore, as described above, the present embodiment is configured as follows. The "flow rate value data" corresponding to the time data such as the "corrected first heartbeat start time data" of the "corrected heartbeat cycle data storage unit 62", is extracted. Based on the stored "difference value data", a degree of the difference (deviation) between the phases is recognized. Therefore, as will be described later, based on the "difference value data" and based on the degree of the difference (deviation) between the phases, the controller 10 corrects the timing (time data) of supplying the blood and stopping the blood supply. In this manner, the correction can be easily performed.

Figure 13:
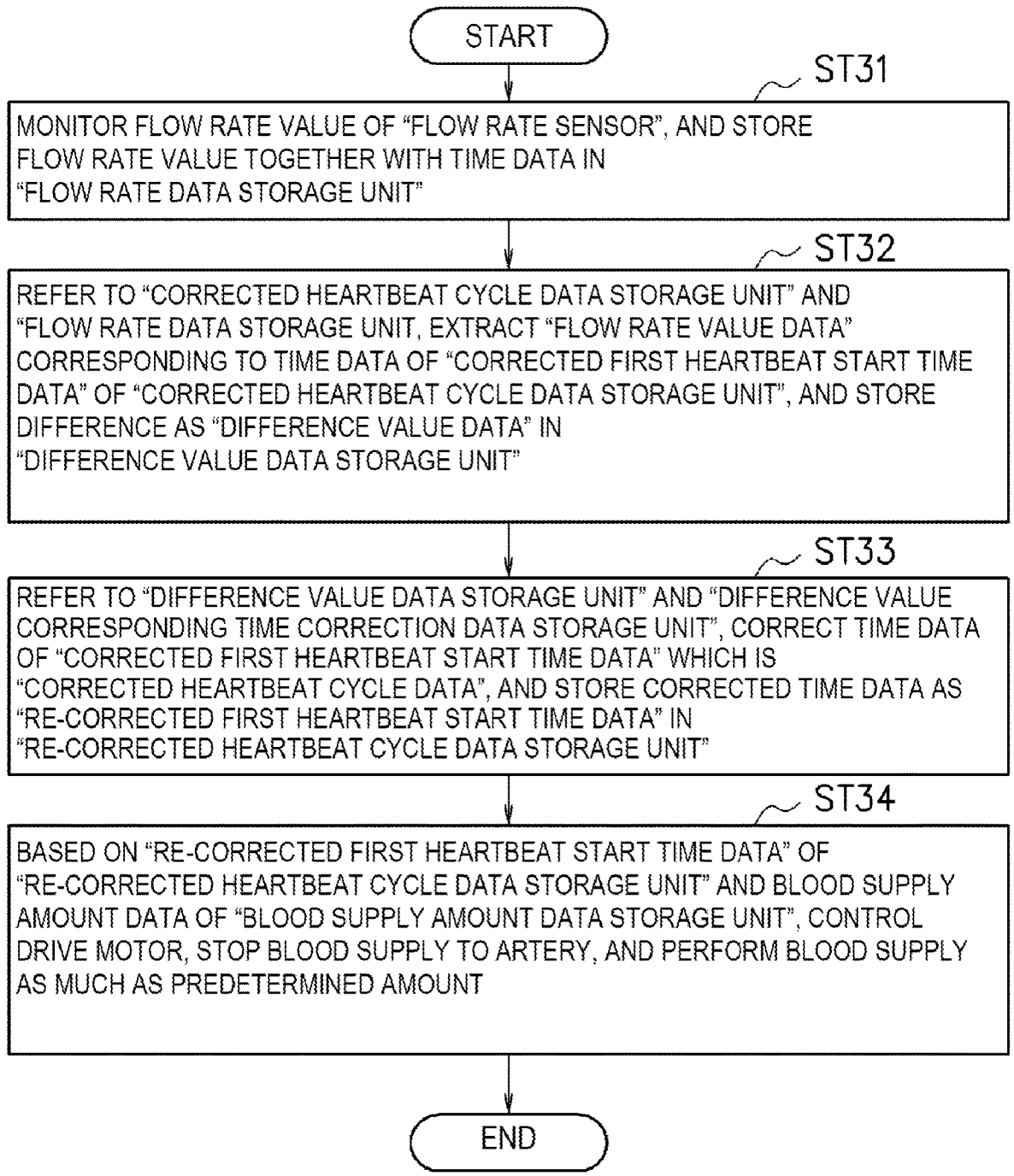
FIG. 13 is still another schematic flowchart illustrating a main operation example of the extracorporeal circulator in FIG. 1.

Hereinafter, ST33 and ST34 in FIG. 13 will be described in detail. First, in ST33, a "re-corrected heartbeat cycle data generation processing unit (program) 73" in FIG. 7 is operated so as to access a "difference value data storage unit 72" in FIG. 7 and a "difference value corresponding time correction data storage unit 74" in FIG. 3. This "difference value corresponding time correction data storage unit 74" stores the corrected time data for resolving the difference value, based on the "difference value data". That is, in order to correct the deviation (difference) between the phases illustrated in FIGS. 17A and 17B, the "corrected time data" based on the "difference value data" is stored.

Figure 8:
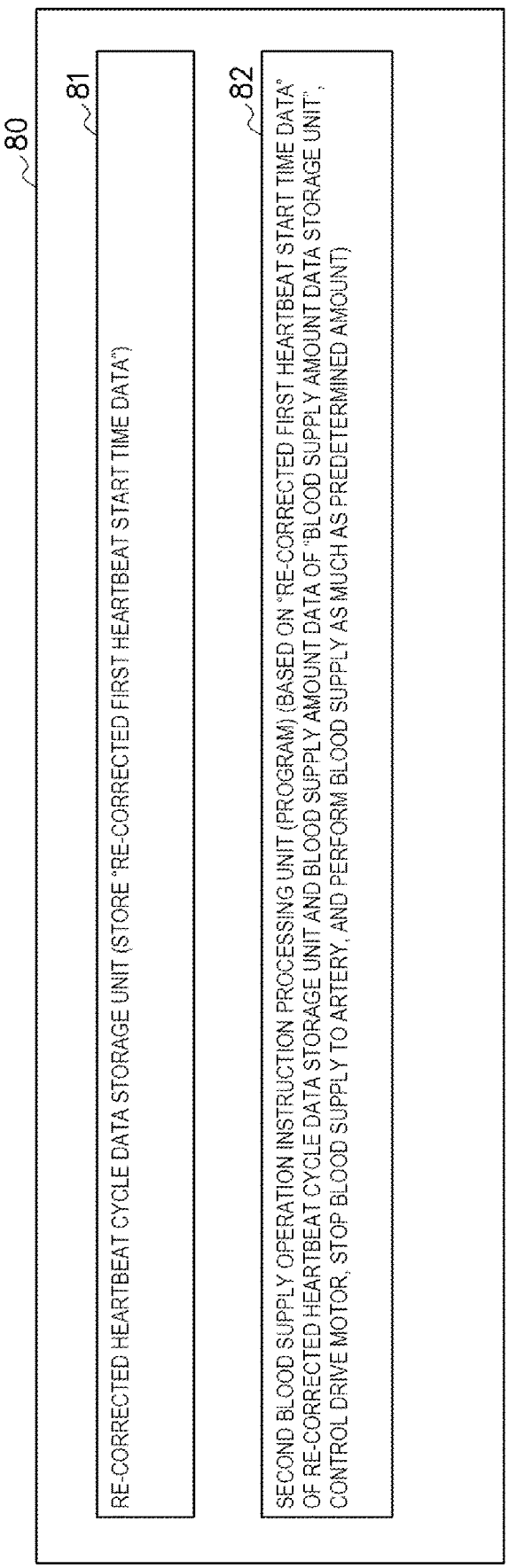
FIG. 8 is a schematic block diagram illustrating a main configuration of a sixth various information storage unit.

Then, the "re-corrected the heartbeat cycle data generation processing unit (program) 73" corrects the time data such as the "corrected first heartbeat start time data" which is the "corrected heartbeat cycle data", as the "corrected time data", and the "re-corrected first heartbeat start time data" is stored in a "re-corrected heartbeat cycle data storage unit 81" in FIG. 8.

Next, the process proceeds to ST34. In ST34, a "second blood supply operation instruction processing unit (program) 82" in FIG. 8 is operated. Based on the "re-corrected first heartbeat start time data", the "re-corrected first heartbeat maximum time data", the "re-corrected second heartbeat start time data", and the "re-corrected second heartbeat maximum time data" of the "re-corrected heartbeat cycle data storage unit 81" in FIG. 8 and the blood supply amount data in the "blood supply amount data storage unit 64" in FIG. 6, the drive motor 4 is controlled so as to alternately stop the blood supply to the artery and to turn on for supplying a predetermined amount of the blood.

In this way, according to the present embodiment, even if the timing of the heartbeat (the "systolic phase" and the "diastolic phase") of the heart of the patient P is changed, the change is recognized. Therefore, an error (deviation) can be adjusted by quickly correcting the timing at which the extracorporeal circulator 1 turns on the blood supply or stops the blood supply.

Incidentally, the present invention is not limited to the above-described embodiment.

What is claimed is:

1. An extracorporeal circulation management device comprising:
 a flow rate measurement unit generating a plurality of flow rate measurements of blood flowing through a blood pump in a closed circuit between an artificial lung and a target person which are sampled in a time series;
 a flow rate information storage unit that stores the plurality of flow rate measurements;
 a heartbeat timing information generation unit that identifies systolic phase candidate information which may potentially correspond to systolic phase information on a systolic phase in which a heart of the target person contracts and diastolic phase candidate information which may potentially correspond to diastolic phase information on a diastolic phase in which the heart expands, based on comparisons between a plurality of the flow rate measurements acquired in time series, wherein blood supply starting and stopping information is transmitted to a motor unit for providing pulsatile operation of the blood pump according to the systolic phase candidate information and the diastolic phase candidate information; and a systolic-diastolic phase correction unit that identifies a corrected systolic phase information and a corrected diastolic phase information in each heartbeat based on the flow rate measurements during the pulsatile operation of the blood pump using the systolic phase candidate information and the diastolic phase candidate information;

wherein the blood supply starting and stopping information transmitted thereafter to the motor unit is based on the corrected systolic phase information and the corrected diastolic phase information.

2. The extracorporeal circulation management device according to claim 1, wherein the heartbeat timing information generation unit compares flow rate measurements in order to identify maximum and minimum sample values, and compares the identified maximum and minimum sample values to threshold value information serving as reference information for the systolic phase information or the diastolic phase information, wherein an identified maximum sample value which is greater than an upper threshold value corresponds to the systolic phase candidate information and an identified minimum sample value which is less than a lower threshold value corresponds to the diastolic phase candidate information.

3. The extracorporeal circulation management device according to claim 2, wherein the flow rate measurements which are compared in order to identify maximum and minimum sample values are comprised of three consecutive flow rate measurements in time series.

4. The extracorporeal circulation management device according to claim 1, wherein the systolic-diastolic phase correction unit determines a difference change information based on a difference among an actual heartbeat, a flow rate measurement coinciding with the systolic phase candidate information and a flow rate measurement coinciding with the diastolic phase candidate information, and wherein the corrected systolic phase information and the corrected diastolic phase information are identified based on the difference change information.

5. An extracorporeal circulator comprising:

an artificial lung unit that performs gas exchange on blood of a target person;

a tube unit that connects the artificial lung unit and the target person to each other in a closed circuit;

a flow measurement unit that generates a plurality of blood flow measurements inside the tube unit;

a blood pump with a motor unit that pumps the blood flowing inside the tube unit; and a management device comprising:

a flow rate information storage unit that stores the plurality of flow rate measurements;

a heartbeat timing information generation unit that identifies systolic phase candidate information which may potentially correspond to systolic phase information on a systolic phase in which a heart of the target person contracts and diastolic phase candidate information which may potentially correspond to diastolic phase information on a diastolic phase in which the heart expands, based on comparisons between a plurality of the flow rate measurements acquired in time series, wherein blood supply starting and stopping information is transmitted to a motor unit for providing pulsatile operation of a blood pump according to the systolic phase candidate information and the diastolic phase candidate information; and a systolic-diastolic phase correction unit that identifies a corrected systolic phase information and a corrected diastolic phase information in each heartbeat based on the flow rate measurements during the pulsatile operation of a blood pump using the systolic phase candidate information and the diastolic phase candidate information;

wherein the blood supply starting and stopping information transmitted thereafter to the motor unit is based on the corrected systolic phase information and the corrected diastolic phase information.

6. The extracorporeal circulator according to claim 5, wherein the management device further comprises:

a blood supply period change information storage unit that stores blood supply period change information for changing a blood supply period of the artificial lung unit, based on a tube unit length which is a length of the tube unit between the artificial lung unit and the target person.

7. A control method of an extracorporeal circulation management device, the control method comprising:

storing a plurality of flow rate measurements of blood flowing through a blood pump and a tube in a closed circuit between an artificial lung and a target person, which is acquired from a flow rate measurement unit, in a flow rate information storage unit;

identifying heartbeat timing information including systolic phase candidate information which may potentially correspond to systolic phase information on a systolic phase in which a heart of the target person contracts and diastolic phase candidate information which may potentially correspond to diastolic phase information on a diastolic phase in which the heart expands, based on comparisons between a plurality of the flow rate measurements acquired in time series;

transmitting blood supply starting and stopping information to a motor unit for providing pulsatile operation of a blood pump according to the systolic phase candidate information and the diastolic phase candidate information;

identifying a corrected systolic phase information and a corrected diastolic phase information in each heartbeat based on the flow rate measurements during the pulsatile operation of the blood pump using the systolic phase candidate information and the diastolic phase candidate information; and thereafter, transmitting the blood supply starting and stopping information to the motor unit based on the corrected systolic phase information and corrected diastolic phase information.

* * * * *